United States Patent [19]

Hung et al.

[11] Patent Number: 4,795,736

[45] Date of Patent: Jan. 3, 1989

[54] NOVEL COMPOUNDS, PROCESS AND MARKING SYSTEMS

[75] Inventors: William M. Hung, Cincinnati, Ohio; James E. Kassner, Maplewood, N.J.

[73] Assignee: Hilton Davis Co., Cincinnati, Ohio

[21] Appl. No.: 56,169

[22] Filed: Jun. 1, 1987

[51] Int. Cl.$^4$ .................... B41M 5/16; B41M 5/18; B41M 5/22

[52] U.S. Cl. .................... 503/218; 427/151; 428/913; 428/914; 503/223

[58] Field of Search ............... 427/150–152; 503/217, 218, 223, 224, 225; 428/913, 914

[56] References Cited

U.S. PATENT DOCUMENTS

| 3,957,288 | 5/1976 | Lemahieu et al. | 503/223 |
|---|---|---|---|
| 3,958,815 | 5/1976 | Poot et al. | 503/223 |
| 4,287,336 | 9/1981 | Petitpierre | 503/218 |

FOREIGN PATENT DOCUMENTS

| 60-231766 | 10/1985 | Japan | 503/218 |
|---|---|---|---|
| 60-230890 | 10/1985 | Japan | 503/218 |

*Primary Examiner*—Bruce H. Hess
*Attorney, Agent, or Firm*—Terrence E. Miesle

[57] ABSTRACT

1-A-1-B-3-(2-$R^2$-4-N-R-N-$R^1$-aminophenyl)-3-(-4-$R^3$-phenylsulfonyl)prop-1-ene useful as color formers, particularly in transfer imaging, pressure-sensitive and thermal-responsive carbonless duplicating systems, are prepared by the interaction of the corresponding 1-A-1-B-ethene with the appropriate 2-$R^2$-4-N-R-N-$4^1$-benzaldehyde and the appropriate 4-$R^3$-benzenesulfinic acid in the presence of an acidic catalyst.

10 Claims, No Drawings

NOVEL COMPOUNDS, PROCESS AND MARKING SYSTEMS

BACKGROUND OF THE INVENTION (a) Field of the Invention

The invention described herein relates to novel compounds classified in the field of organic chemistry as propenes, useful as color-forming substances, particularly in the art of transfer imaging, pressure-sensitive and thermal-responsive carbonless duplicating; to transfer imaging systems containing said compounds; to pressure-sensitive and thermal-responsive carbonless duplicating systems containing said compounds and to processes for preparing said propenes.

(b) Information Disclosure Statement

Several classes of organic compounds of widely diverse structural types are known to be useful as colorless precursors for transfer imaging systems. Among the more important classes, there may be named leuco-type dyestuffs such as: phthalides, for example, crystal violet lactone, Malachite green lactone; fluorans, for example, 3-dialkylamino-7-dialkylaminofluoran, 3-dimethylamino-6-methoxyfluoran; phenothiazines, for example, benzoyl leuco methylene blue; Rhodamines, for example, Rhodamine B-anilinolactone; and spirodinaphthopyrans, for example, 3-methyl-spiro-dinaphthopyran. The classes of organic compounds listed above also generally find utility in pressure-sensitive and thermal-responsive carbonless duplicating systems.

Typical of the transfer imaging systems, is the system described in U.S. Pat. No. 4,399,209, which issued Aug. 16, 1983. In this patent, a transfer imaging system is disclosed wherein images are formed by image-wise exposing a layer comprising a chromogenic and pressure-rupturable material containing as an internal phase, a photosensitive composition. In this system, the chromogenic material is encapsulated with the photosensitive compound. Upon exposure to filtered U.V. or blue light in the wavelength range of 380 to 480 nanometers, a certain portion of the capsules will harden. The capsules in which the internal phase has remained liqid are ruptured and the chromogenic material is image-wise transferred to a developer or copy sheet where the chromogenic material reacts with a developer to form an image.

Typical of the many commercially accepted pressure-sensitive and thermal-responsive carbonless copy systems are those described in U.S. Pat. Nos. 2,712,507; 2,800,457; 3,041,289; and 4,000,087, which issued July 5, 1955; July 23, 1957; June 26, 1962; and Dec. 28, 1976, respectively.

Many of the color formers in the prior art suffer one or more disadvantages such as low tinctorial strength, low resistance to sublimation, low susceptibility to copiability of the color-developed images in standard office copying machines, for example, a xerographic type of copier, poor image stability in the presence of light, i.e., the product image fades losing intensity or changes to a less acceptable color, and low solubility in common organic solvents. The latter disadvantage requires the use of specialized and expensive solvents in order to obtain microencapsulated solutions of sufficient concentration for use in pressure-sensitive copying systems and transfer imaging systems.

The following items to date appear to constitute the most relevant prior art with regard to the instant invention.

Ricoh KK-owned Japanese Patent Publication No. 60,231,766, which was published Oct. 18, 1985, discloses compounds having the structural formula

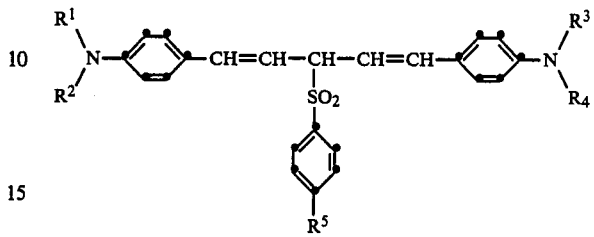

wherein $R^1$–$R^4$ = lower alkyl; and $R^5$ = H or lower alkyl. The compounds are disclosed as being useful as color formers for heat and pressure-sensitive recording paper capable of being read by an optical reader.

Ricoh KK-owned Japanese Patent Publication No. 60,230,890, which was published Oct. 16, 1985, discloses compounds having the structural formula

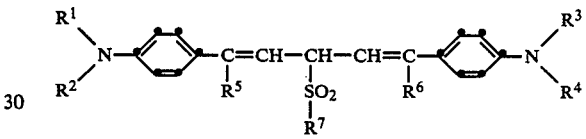

wherein $R^1$–$R^4$ are H or (un)substituted alkyl; $R^5$ and $R^6$ are H or (un)substituted phenyl; $R^7$ is (un)substituted alkyl or (un)substituted phenyl.

The compounds are disclosed as being useful as color formers for heat- and pressure-sensitive recording paper capable of being read by an optical reader.

SUMMARY OF THE INVENTION

In its composition of matter aspect, the invention relates to certain 1-A-1-B-3-(2-$R^2$-4-N-R-N-$R^1$-aminophenyl)-3-(4-$R^3$-phenylsulfonyl)prop-1-e useful in transfer imaging systems, pressure-sensitive and thermal-responsive carbonless duplicating systems.

In its process aspect, the invention relates to a process for producing 1-A-1-B-3-(2-$R^2$-4-N-R-N-$R^1$-aminophenyl)-3-(4-$R^3$-phenyl-sulfonyl)prop 1-A 1-B-ethene with the appropriate 2-$R^2$-4-N-R-N-$R^1$-benzaldehyde and the appropriate 4-$R^3$-benzenesulfinic acid in the presence of an acidic catalyst.

The present invention provides in one of its article of manufacture aspects, a substrate for use in transfer imaging systems comprising a support sheet containing as a color-forming substance, 1-A-1-B-3-(2-$R^2$-4-N-R-N-$R^1$-aminophenyl)-3-(4-$R^3$-phenylsulfonyl)prop-1-enes.

The present invention provides in the second of its article of manufacture aspects, a substrate for use in pressure-sensitive and the mal-responsive carbonless duplicating systems comprising a supPort sheet containing as a color-forming substance, 1-A-1-B-3-(2-$R^2$-4-N-R-N-$R^1$-aminophenyl)-3-(4-$R^3$-phenylsulfonyl)prop-1-enes.

DETAILED DESCRIPTION INCLUSIVE OF THE PREFERRED EMBODIMENTS

More specifically, this invention in one of its composition of matter aspects, resides in the novel 1-A-1-B-3-

(2-$R^2$-4-N-R-N-$R^1$-aminophenyl)-3-(4-$R^3$-phenylsulfonyl)prop-1-enes having the formula

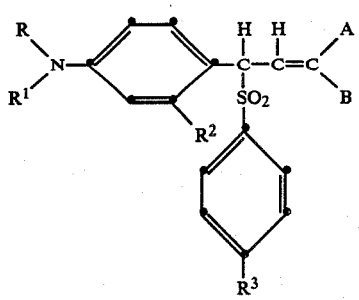

FORMULA I wherein A represents a moiety selected from the group consisting of

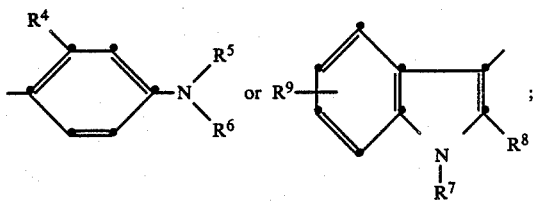

B represents a moiety selected from the group consisting of

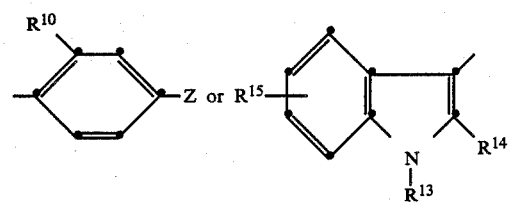

in which Z represents hydrogen or —$NR^{11}R^{12}$; R, $R^5$ and $R^{11}$ independently represent hydrogen; non-tertiary $C_1$ to $C_{16}$ alkyl; phenyl; phenylssubstituted by one or two of non-tertiary $C_1$ to $C_4$ alkyl, non-tertiary $C_1$ to $C_4$ alkoxy, nitro or halo, benzyl; or benzyl substituted in the benzene ring by one or two of non-tertiary $C_1$ to $C_4$ alkyl, non-tertiary $C_1$ to $C_4$ alkoxy, nitro or halo; $R^1$, $R^6$ and $R^{12}$ independently represent non-tertiary $C_1$ to $C_{16}$ alkyl; $R^2$, $R^4$ and $R^{10}$ independently represent hydrogen, non-tertiary $C_1$ to $C_{16}$ alkyl, non-tertiary $C_1$ to $C_8$ alkoxy, nitro or halo; $R^3$ represents hydrogen, non-tertiary $C_1$ to $C_{16}$ alkyl, non-tertiary $C_1$ to $C_4$ alkoxy, nitro or halo; $R^7$ and $R^{13}$ independently represent hydrogen; non-tertiary $C_1$ to $C_{16}$ alkyl unsubstituted or substituted by non-tertiary $C_1$ to $C_{16}$ alkoxy, phenoxy, phenyl, phenyl substituted by one or two of non-tertiary $C_1$ to $C_4$ alkyl, non-tertiary $C_1$ to $C_4$ alkoxy, nitro or halo; $R^8$ and $R^{14}$ independently represent hydrogen, non-tertiary $C_1$ to $C_4$ alkyl or phenyl; $R^9$ and $R^{15}$ independently represent one or two of hydrogen, non-teritary $C_1$ to $C_4$ alkyl, non-tertiary $C_1$ to $C_4$ alkoxy, nitro or halo; and wherein R and $R^1$ together with the nitrogen represent piperidinyl or pyrrolidinyl.

In a first particular embodiment within the ambit of the compsition of matter aspect are the novel 1-(2-$R^4$-4-N-$R^5$-N-$R^6$-amioophenyl)-1-(2-$R^{10}$-4-Z-aminophenyl)-3-(2-$R^2$-4-N-R-N-$R^1$-aminophenyl)proP-1-enes of Formula I wherein A is (2-$R^4$-4-N-$R^5$-N-$R^6$-aminophenyl) and B is (2-$R^{10}$-4-Z-aminophenyl) having the formula

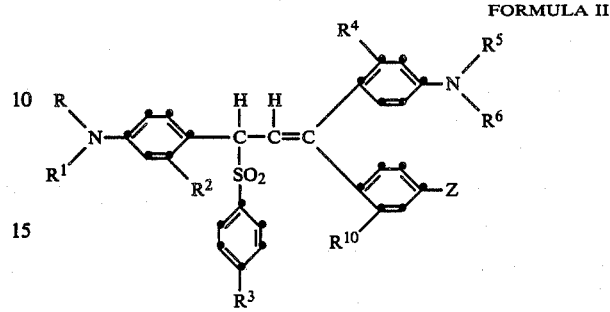

FORMULA II

Formula II in which Z, R, $R^1$, $R^2$, $R^3$, $R^4$, $R^5$, $R^6$, and $R^{10}$ have the same respective meanings given in Formula I.

In a second particular embodiment within the ambit of the composition of matter aspect are the novel 1-(2-$R^4$-4-N-$R^5$-N-$R^6$-aminophenyl)-1-(1-$R^{13}$-2-$R^{14}$-5/6-$R^{15}$-indol-3-yl)-3-(2-$R^2$-4-N-R-N-$R^1$-aminophenyl)-3-(4-$R^3$-phenylsulfonyl)prop-1-enes of Formula I wherein A is (2-$R^4$-4-N-$R^5$-N-$R^6$-aminophenyl) and B is (1-$R^{13}$-$2R^{14}$-5/6-$R^{15}$-indol-3-yl) having the formula

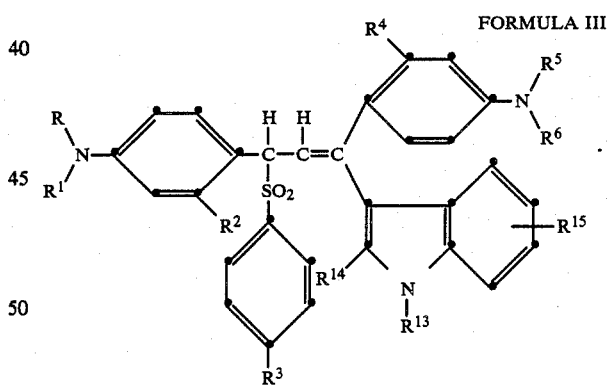

FORMULA III in which R, $R^1$, $R^2$, $R^3$, $R^4$, $R^5$, $R^6$, $R^{13}$, $R^{14}$, and $R^{15}$ have the same respective meanings given in Formula I.

In a third particular embodiment within the ambit of the composition of matter aspect are the novel 1--(1-$R^7$-2-$R^8$-5/6-$R^9$-indol-3-yl)-1-(1-$R^{13}$-2-$R^{14}$-5/6-$R^{15}$-indol-3-yl)-3-(2-$R^2$-4-N-R-N-$R^1$-aminophenyl)-3-(4-$R^3$-phenylsulfonyl)prop-1-enes of Formula I wherein A is (1-$R^7$-2-$R^8$-5/6-$R^9$-indol-3-yl) and B is (1-$R^{13}$-$2R^{14}$-5/6-$R^{15}$-indol-3-yl) having the formula

FORMULA IV

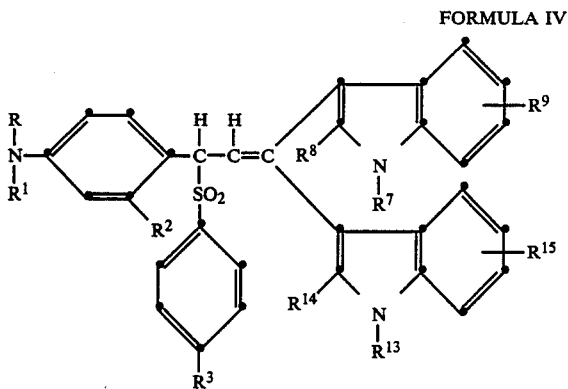

in which R, $R^1$, $R^2$, $R^3$, $R^7$, $R^8$, $R^9$, $R^{13}$, $R^{14}$, and $R^{15}$ have the same respective meanings given in Formula I.

In its process aspect, the invention sought to be patented resides in the process for preparing a 1-A-1-B-3-(2-$R^2$-4-N-R-N-$R^1$-aminophenyl)-3-(4-$R^3$-phenylsulfonyl)prop-1-ene according to Formula I which comprises interacting the corresponding 1-A-1-B-ethene with the appropriate 2$R^2$-4-N-R-N-$R^1$-aminobenzaldehyde and the appropriate 4-$R^3$-benzene sulfinic acid in the presence of an acidic catalyst in which A, B, R, $R^1$, $R^2$, and $R^3$ have the same respective meanings given in Formula I.

In one of its article of manufacture aspects, the invention sought to be patented resides in a substrate for use in transfer imaging comprising a support sheet coated with a layer containing as a color-forming substance a 1-A-1-B-3-(2-$R^2$-4-N-R-N-$R^1$-aminophenyl)-3(4-$R^3$-phenylsulfonyl)prop-1-ene according to Formula I wherein A, B, R, $R^1$, $R^2$, and $R^3$ have the same respective meanings given in Formula I.

In a particular embodiment in accordance with its first article of manufacture aspect, the invention sought to be patented resides in a substrate for use in transfer imaging comprising a support sheet coated with a layer containing as a color-forming substance a 1-(2-$R^4$-4--N-$R^5$-N-$R^6$-aminophenyl)-1-(2-$R^{10}$-N-$R^{11}$-N-$R^{12}$-aminophenyl)-3-(2$R^2$-4-N-R-N-Rl-aminophenyl)-3-(4-$R^3$-phenylsulfonyl)prop-1-ene according to Formula II wherein R, $R^1$, $R^2$, $R^3$, $R^4$, $R^5$, $R^6$, $R^{10}$, $R^{11}$, and $R^{12}$ have the same respective meanings given in Formula II.

In a second particular embodiment in accordance with its first article of manufacture aspect, the invention sought to be patented resides in a substrate for use in transfer imaging comprising a support sheet coated with a layer containing as a color-forming substance a 1-(2-$R^4$-4-N-$R^5$-N-$R^6$-aminophenyl)-1-(1-$R^{13}$-2-$R^{14}$-5 /6-$R^{15}$-indol-3-yl)-3-(2-$R^2$-4-N-R-N-$R^1$-aminophenyl)-3-(4-$R^3$-phenylsulfonyl)prop-1-according to Formula III wherein R, $R^1$, $R^2$, $R^3$, $R^4$, $R^5$, $R^6$ $R^{13}$, $R^{14}$, and $R^{15}$ each have the same respective meanings given in Formula III.

In a third particular embodiment in accordance with its first article of manufacture aspect, the invention sought to be patented resides in a substrate for use in transfer imaging comprising a support sheet coated with a layer containing as a color-forming substance a 1-(1 -$R^7$-2-$R^8$-5/6-$R^9$-indol-3-yl)-1-(1-$R^{13}$-2-$R^{14}$-5/6-$R^{15}$-indol-3-yl)-3-(2-$R^2$-4-N-R-N-$R^1$-aminophenyl)-3-(4-$R^3$-phenylsulfonyl)prop-1-ene according to Formula IV wherein R, $R^1$, $R^2$, $R^3$, $R^7$, $R^8$, $R^9$, $R^{13}$, $R^{14}$, and $R^{15}$ each have the same respective meanings given in Formula IV.

In a second of its article of manufacture aspects, the invention sought to be patented resides in a substrate for use in a pressure-sensitive or thermal-responsive marking system comprising a support sheet coated with a layer containing as a color-forming substance a 1-A-1-B-3-(2-$R^2$-4-N-R-N-$R^1$-aminophenyl)-3-(4-$R^3$-phenylsulfonyl)prop-1-ene according to Formula I wherein A, B, R, $R^1$, $R^2$, and $R^3$ have the same respective meanings given in Formula I.

In a particular embodiment in accordance with its second article of manufacture aspects, the invention sought to be patented resides in a substrate for use in a pressure-sensitive or a thermal-responsive marking system comprising a support sheet coated with a layer containing as a color-forming substance a 1-(2-$R^4$-4-N-$R^5$-N-$R^6$-aminophenyl)-1-(2-$R^{10}$-4-N-$R^{11}$-N-$R^{12}$-aminophenyl)-3-(2-$R^2$-4-N-R-N-$R^1$-aminophenyl)-3-(4-$R^3$-phenylsulfonyl)prop1-ene according to Formula II wherein R, $R^1$, $R^2$, $R^3$, $R^4$, $R^5$, $R^6$, $R^{10}$, $R^{11}$, and $R^{12}$ have the same respective meanings given in Formula II.

In a second particular embodiment in accordance with its second article of manufacture aspects, the invention sought to be patented resides in a substrate for use in a pressure-sensitive or a thermal-responsive marking system comprising a support sheet coated with a layer containing as a color-forming substance a 1-(2-$R^4$-4-N-$R^5$-N-$R^6$-aminophenyl)-1-(1-$R^{13}$-2-$R^{14}$-5/6-$R^{16}$-indol- 3-yl)-3-(2-$R^2$-4-N-R-N-$R^1$-aminophenyl)-3-(4-$R^3$-phenylsulfonyl)prop-1-ene according to Formula III wherein R, $R^1$, $R^2$, $R^3$, $R^4$, $R^5$, $R^6$, $R^{13}$, $R^{14}$, and $R^{15}$ have the same respective meanings given in Formula III.

In a third particular embodiment in accordance with its second article of manufacture aspects, the invention sought to be patented resides in a substrate for use in a pressure-sensitive or thermal-responsive marking system comprising a support sheet coated with a layer containing as a color-forming substance a 1-(1-$R^7$ -2-$R^8$-5/6-$R^9$-indol-3-yl)-1-(1-$R^{13}$-2-$R^{14}$-5/6-$R^{15}3$-yl)-3-(2-$R^2$-4-N-R-N-$R^1$-aminophenyl)-3-(4-$R^3$-phenylsulfonyl)prop-1ene according to Formula IV wherein R, $R^1$, $R^2$, $R^3$, $R^7$, $R^8$, $R^9$, $R^{13}$, $R^{14}$, and $R^{15}$ have the same respective meanings given in Formula IV.

In a fourth particular embodiment in accordance with its second article of manufacture aspects, the invention sought to be patented resides in a pressure-sensitive transfer sheet, adapted for use with a receiving sheet having an electron-accepting layer, comprising a support sheet coated on one side with a layer of pressure-rupturable microcapsules, said microcapsules containing a liquid solution of a color-forming substance comprising at least one compound having Formula I.

In a fifth particular embodiment in accordance with its second article of manufacture aspects, the invention sought to be patented resides in a thermal-responsive record material comprising a support sheet coated on one side with a layer containing a mixture comprising at least one color-forming compound having Formula I and an acidic developer arranged such that application of heat will produce a mark-forming reaction between the color-forming compound and the acidic developer.

As used herein the terms "non-tertiary $C_1$ to $C_4$ alkyl", "non-tertiary $C_1$ to $C_8$ alkyl" and "non-tertiary $C_1$ to $C_{16}$ alkyl" denote saturated monovalent straight or branched aliphatic hydrocarbon radicals including methyl, ethyl, propyl, isopropyl, butyl, isobutyl, amyl, 1-methylbutyl, 3-methylbutyl, hexyl, isohexyl, heptyl, isoheptyl, octyl, isooctyl, n-doceyl, and the like.

The term "non-tertiary $C_1$ to $C_4$ alkoxy" includes saturated acyclic, straight or branched-chain groups such as methoxy, ethoxy, propoxy, isopropoxy, butoxy, sec-butoxy and isobutoxy.

As used herein the terms "halo" and "halogen" include chloro, fluoro, bromo, and iodo. Chloro is the preferred halo substituent because of the relatively low cost and ease of preparation of the required chloro-substituted intermediates and because the other halogens offer no particular advantages over chloro. However, the other above-named halo substituents are also satisfactory.

The compounds of Formula I hereinabove are essentially colorless in the depicted form. When contacted with a color developer such as those conventionally employed in carbonless duplicating systems which are generally acidic in nature, the compounds of Formula I develop purple, blue, an cyan colored images. Illustrative of specific examples of these color developers are clay minerals such as acid clay, active clay, attapulgite, and silton clay; organic acids such as tannic acid, gallic acid, propyl gallate, and so forth; acid polymers such as phenol-formaldehyde resins, phenol acetylene condensation resins, condensates between an organic carboxylic acid having at least one hydroxy group and formaldehyde, and so forth; metal salts or aromatic carboxylic acids such as zinc salicylate, tin salicylate, zinc 2-hydroxy naphthoate, znnc 3,5-di-tertiary-butyl salicylate, oil soluble metal salts of phenol-formaldehyde novolak resins, and so forth. These color developers are also useful in transfer imaging systems. The developed images are very insensitive to light, are of good tinctorial strength, possess excellent xerographic copiability and enhanced solubility in common organic solvents. The compounds are thus highly suitable for use as colorless precursors. that is. color-forming substances in pressure-sensitive carbonless duplicating systems. The compounds of Formula I can be used alone as color formers to produce images which are readily copiable, or can be used as toners to admixture with other color formers to produce images of neutral shade which desirably are readily copiable by xerographic means.

The compounds of Formula I may be incorporated into transfer imaging systems which refer to office based systems suitable for making photocopies. One such system is disclosed in U.S. Pat. No. 4,399,209. In this system, the color-forming phthalides of Formula I are microencapsulated together with a photo-initiator in a photo-sensitive composition in pressure-rupturable capsules. The microcapsules are then coated onto a surface of a substrate. Images are formed by image-wise exposing the encapsulated eearing substrate to actinic radiation and rupturing the capsules in the presence of a developer to obtain an image.

The compounds of this invention may be incorporated in any of the commercially accepted systems known in the carbonless duplicating art. A typical technique for such applications is as follows. Solutions containing one or more colorless compounds of Formula I optionally in admixture with other color formers, in suitable solvents, are microencapsulated by well known procedures, for example, as described in U.S. Pat. Nos. 3,369,649; 3,429,827; and 4,000,087. The microcapsules are coated on the reverse side of a sheet with the aid of a suitable binder and the coated transfer sheet is then assembled in a manifold with the microcapsule coated side in contact wihh a receiving sheet coated with an electron-accepting substance, for example, silton clay or a phenolic resin. Application of pressure to the manifold, such as that exerted by a stylus, typewriter, or other form of writing or printing, causes the capsules on the reverse side to rupture. The solution of the color formers released from the ruptured microcapsules flows to the receiving sheet and, on contact with the acidic medium thereon, forms purple, blue, and cyan-colored images of good tinctorial strength. It is, of course, obvious that variants of this mode of application can be utilized. For example, the receiving sheet in a manifold can alternatively be coated with the subject compounds and the acidic developing agent can be contained in microcapsules applied to the reverse side of the top sheet in the manifold, or the receiving sheet can be coated with a mixture containing both the acidic developing agent and the microencapsulated color former.

It has also been found that when the compounds of Formula I are intimately mixed with an acidic developer, for example, Bisphenol A of the type generally employed in thermal papers such as described in U.S. Pat. No. 3,539,375, that is, papers which produce a colored image when contacted with a heated stylus or heated type, heating of said mixture rroduces a colored image of varying shades from purple to cyan depending on the particular compound of the invention employed. The ability of the compounds of Formula I to form a deep color when heated in admixture with an acidic devsloper such as Bisphenol A, makes them useful in thermal paper marking systems, either where an original or a duplicate copy is prepared by contacting the thermal paper with a heated stylus or heated type in any of the methods generally known in the art.

The compounds of Formula I, having an ethenyl linkage, have beein found to exhibit light absorption in their colored form at wavelengths nearer to the infrared then do similar compounds without the ethenyl moieties. It is an object of this invention to provide compounds possessing both near infrared color response and chromogenic properties when the compounds are incorporated into a pressure-sensitive or thermal-rsspon-sive carbonless duplicating system and transfer imaging system involving reactive contact with a color-activating material to develop dark colored images in areas where the marking is desired. The developed colored images of the compounds of Formula I absorbing at or near the infrared wavelengths especially relate to providing a color which is particularly visible to machine readers and copiers, such as the optical character reading machines. The various optical character or mark reading machines are used for reading the record images developed on a recording material. Generally the developed images on the conventional recording materials are those which can be read by the optical reading machines which are capable of reading for the visible wavelength range of 500 nm to 880 nm. One example of record material which is used and in which the compounds of Formula I find use in carbonless duplicating systems and image transfer systems is the use of business forms.

The best mode contemplated by the inventors of carrying out this invention will now be described so as to enable any person skilled in the art to which it pertains to make and use the same.

In accordance with the aforementioned process aspect of this invention, the compounds of Formula I are obtained by reacting one molecular proportion of a 1-A-1-B-ethene with one molecular proportion of a 2-$R^2$-4-N-R-N-$R^1$-benzaldehyde and one molecular proportion of a 4-$R^3$-benzenesulfinic acid which is conveniently added to the reaction as an alkali metal salt such as the sodium salt. The reaction is conveniently carried out in an aliphatic alcohol, for example, ethanol or propanol in the approximate temperature range of from 60° C. to the reflux temperature of the reaction mixture from approximately three hours to approximately forty-eight hours. The propenes of Formula I thus obtained can be isolated by several methods. One such method of isolation is to pour the reaction mixture into ice water and to filter the propenes from the mixture. An alternative method of isolation is to pour the reaction mixture into a mixture of water immiscible organic liquid in which the propenes are soluble, such as toluene and ice water. The organic liquid layer containing the propenes is separated from the aqueous layer and the propene is isolated by removing the organic liquid by evaporation or distillation. The propene, once isolated, can be purified by conventional means such as trituration or recrystallization from a suitable solvent and then collected by filtration. Purification can also be effected by column chromatography. The propene to be purified is dissolved in a suitable organic liquid or combination of organic liquids and the solution is passed through a chromatography column which has been packed with a suitable substrate, for example, silica gel, cellulose, alumina, and the like. Numerous fractions are collected and analyzed to determine fraction(s) containing the desired propene. The fraction(s) which contain the desired product are then combined (if more than one) and concentrated to obtain the propene which is then collected by filtration.

The requisite 1-A-1-B-ethenes required in the practice of this invention are the subject of a separate patent application. The 1-A-1-B-ethenes wherein A is a 1-$R^7$-2-$R^8$-5/6-$R^9$-indol-3-yl and B is a 1-$R^{13}$-2-$R^{14}$-5/6-$R^{15}$-indol-3-yl are conveniently prepared by interacting one molecular proportion of a 1-$R^7$-2-$R^8$-5/6-$R^9$-indole and one molecular proportion of a 1-$R^{13}$-2-$R^{14}$-5/6-$R^{15}$-indole with one molecular proportion of acetic anhydride. The reaction is conveniently carried out in excess acetic anyydride at a temperature in the range of room temperature to 90° C. for from approximately two hours to approximately twenty hours in the presence of an acidic catalyst, such as methanesulfonic acid. The product thus obtained can be isolated by pouring the reaction mixture into an aqueous base, such as ammonium hydroide, sodium hydroxide, potassium hydroxide, sodium carbonate, or sodium bicarbonate, and the product extracted with a water-immiscible organic liquid, such as toluene, xylene, or chlorobenzene, followed by evaporation of the organic liquid leaving the product as a residue. The product, once isolated, can be purified by conventional means, such as trituration or recrystallization, from a suitable organic liquid or by a vacuum distillation. Alternatively, the product thus obtained can be isolated by pouring an organic liquid such as isopropylaalcohol into the reaction mixture and filtering the desired product.

The 1-A-1-B-ethenes wherein A is 2-$R^4$-4-N-$R^5$-N-$R^6$-aminophenyl and B is 1-$R^{13}$-2-$R^{14}$-5/6-$R^{15}$-indol-3-yl are conveniently prepared by interacting one molecular proportion of a 1-$R^{13}$-2-$R^{14}$-5/6-$R^{15}$-indole with one molecular proportion of the appropriate 2-$R^4$-4-N-$R^5$-N-$R^6$-aminoacetophenone. The reaction is conveniently carried out in an organic liquid, such as ethyl alcohol, 2-ethoxyethyl alcohol, isopropyl alcohol, and the like, in the presence of an acidic catalyst, such as methanesulfonic acid, hydrochloric acid hydrobromic acid, or acetic acid, at a temperature in the range of room temperature to the reflux temperature of the organic liquid for from approximately eight hours to approximately thirty hours. The product thus obtained can be isolated and purified, if needed, in a manner identical to the process aspect discussed directly above.

Throughout this application where the possibility of different isomeric products exist, the nomenclature "5/6" is adopted meaning the product obtained or claimed is either a mixture of isomers or one of the two isomers.

The indoles represented by the formulas 1-$R^7$-2-$R^8$-5/6-$R^9$-indole and 1-$R^{13}$-2-$R^{14}$-5/6-$R^{15}$-indole in which 5/6 refers to a substituent in the 5 and/or 6-position of the benzene ring of the indole and, which are required for the interaction with acetic anhydride and the acetophenones to obtain the propenes of Formula I form an old and well known class of compounds readily obtained by conventional procedures well known in the art. The following list of compounds exemplifies indoles which are useful in the practice of the step in the Processes of this invention for producing the aforesaid propenes of Formula I. Indole, 1-methylindole, 2-methylindole, 1,2-dimethylindole, 1-ethyl-2-methylindole, 2-phenylindole, 1-propyl-2-methylindole, 1-benzyl-2-methylindole, 1-butyl-2-methylindole, 1-octyl-2-methylindole, 2-ethyl-5-methylindole, 1-benzyl-5-fluoroindole, 1-methyl-6-nitroindole, 5-methoxy-1-butylindole, 1-allyl-2-methylindole, 1,2-dimethyl-6-nitroindole, 1-(4-chlorobenzyl)-2-methyl-5-nitroindole, 2-ethylindole, 2-ethyl-1-methylindole, 1-isopropylindole, 2-isopropylindole, 1-methyl-5-bromo-6-nitroindole, 2,5,6-trimethylindole, 1-isobutyl-2-methylindole, 6-bromo-2-methylindole, 1-hexylindole, 1-(2,5-dimethylbenzyl)-2-methylindole, 2-propylindole, 6-chloro-2-phenylindole, 1-(2-ethylhexyl)-2-methylindole, 1-(2,6-dichlorobenzyl)-2-methylindole, -vinyl-2-methylindole, 2-ethyl-6-methylindole, 6-fluoro-1-benzylindole, 1-(4-bromobenzyl)-2-isopropylindole, 1-(3-chlorobenzyl)-2-ethylindole, 5-chloro-1-benzylindole, 1-(2-fluorobenzyl)-2-methylindole, 5-iodo-1-(1-methylhexyl)indole, 5,6-dimethoxyindole, 1-(2-methylbenzyl)-2-methylindole, 5,6-dichloro-2-phenylindole, 1-isoamylindole, 1-[3-(2-methyl)-1-Propenyl]-2-methylindole, 1-methoxyethyl-2-methylindole, 1-dodecyl-2-methylindole, 1-tetradecyl-2-methylindole, 1-hexadecyl-2-methylindole, 1-decyl-2-phenylindole, 1-heptyl-2-ethylindole, 1-nonyl-2-propylindole, and 1-phenoxyethyl-2-methylindole.

The molecular structures of the compounds were assigned on the basis of the modes of synthesis and a study of their infrared and nuclear magnetic resonance spectra.

The following examples will further illustrate the invention without, however, limiting it thereto.

EXAMPLE 1

A mixture of 9.0 g of 4-N,N-dimethylaminobenzaldehyde, 16.2 g of 1,1-bis(4-N,N-dimethylaminophenyl)ethene, 15.0 g of sodium methylbenzenesulfinate monohydrate, 225.0 ml of 3A ethanol, and 18.0 ml of concentrated hydrochloric acid was maintained at reflux temperature for approximately sixteen hours. The mixture was cooled to room temperature and poured into an agitated mixture of 750.0 ml of toluene and 1,000 ml of water. The toluene layer was separated and washed with water, then with saturated sodium chloride solution and separated. The toluene was evaporated under vacuum to leave a residue which was crystallized from a mixture of isopropanol and hexane to give 6.64 g of 1,1-bis(4-N,N-dimethylaminophenyl)-3-(4-N,N-dimethylaminophenyl)-3-(4-methylbenzenesulfonyl)propene (Formula II: R, $R^1$, $R^3$, $R^5$, $R^6$=$CH_3$; $R^2$, $R^4$, $R^{10}$=H;Z=N($CH_3$)$_2$), a pale green solid with a melting point of 210° to 213° C. Significant identifying infrared absorption maxima occurred at 1886 cm$^{-1}$, 1750 cm$^{-1}$, 1600 cm$^{-1}$, 1150 cm$^{-1}$, and 820 cm$^{-1}$. Nuclear magnetic resonance was consistent with the assigned structure. When spotted from an acetone solution onto phenolic resin, acid clay, or organic and coated papers, blue-colored images were produced. An acetone solution of the product and Bishenol A was coated onto a glass plate and allowed to dry. The transmission spectrum of the coating had significant adsorption at 730 and 775 nanometers.

EXAMPLE 2

In a manner similar to that given in Example 1, 3.3 g of 4-N,N-diethylaminobenzaldehyde was reacted with 5.4 g of 1,1-bis(4-N,N-dimethylaminophenyl)ethene, 5.0 g of sodium 4-methylbenzenesulfinate monohydrate in 75.0 ml of 3A ethanol and 6.0 ml concentrated hydrochloric acid for approximately 8.5 hours at reflux temperature. There was obtained, 2.4 g of 1,1-bis(4-N,N-dimethylaminophenyl)-3-(4-N,N-diethylaminophenyl)-3-(4-methylbenzenesulfonyl)prop-1-ene. (Formula II: R, $R^1$=$C_2H_5$; $R^2$, $R^4$, $R^{10}$=H; $R^3$, $R^5$, $R^6$;Z=N($CH_3$)$_2$, a pale blue solid which melted at 174° to 177° C. Identifying infrared absorption maxima appeared at 1875 cm$^{-1}$ (weak), 1610 cm$^{-1}$, 1150 cm$^{-1}$, and 820 cm$^{-1}$. This product formed cyan-colored images when spotted from an acetone solution onto phenolic resin, acid clay, or organic acid coated papers. An acetone solution of the product and Bisphenol A was coated onto a glass plate and dried. The transmission spectrum of the coating had significant adsorptions at 727 and 762 nanometers.

EXAMPLE 3

Following the procedure described in Example 1, 3.0 g of 4-N,N-dimethylaminobenzaldehyde, 5.4 g of 1,1-bis(4-N,N-diethylaminophenyl)ethene, 5.0 g of sodium 4-methylbenzenesulfinate monohydrate, 75.0 ml of 3A ethanol, and 6.0 ml of concentrated hydrochloric acid were interacted for approximately nineteen and one-half hours at reflux temperature to obtain 0.87 g of 1,1-bis(4-N,N-diethylaminophenyl)-3-(4-N,N dimethylaminophenyl)-3-(4-methylbenzenesulfonyl)prop-1-ene (Formula II: R, $R^1$, $R^3$=$CH_3$; $R^2$, $R^4$, $R^{10}$=H; $R^5$, $R^6$$C_2H_5$; Z=N($C_2H_5$)$_2$ a pale green solid which melted at 182° to 184° C. with identifying infrared absorption maxima at 1610 cm$^{-1}$, 1150 cm$^{-1}$, and 820 cm$^{-1}$. When spotted from acetone solution onto phenolic resin, acid clay, or organic acid coated paper, turquoise-colored images were produced. An acetone solution of the product and Bisphenol A was coated onto a glass plate and dried. The transmission spectrum of the coating had significant adsorptions at 725 and 750 nanometers.

EXAMPLE 4

Proceeding in a manner similar to that described in Example 1 above, 3.0 g of 4-dimethylaminobenzaldehyde, 5.3 g of 1,1-bis(4-dimethylaminophenyl)ethene, and 5.0 g of sodium 4-methylbenzenesulfinate monohydrate was interacted in a mixture of 100.0 ml of ethanol and 7.0 ml of concentrated hydrochloric acid to obtain 5.59 g of 1,1-3-tris(4-dimethylaminophenyl)-3-(4-methylphenylsulfonyl)prop-1-ene (Formula II:RR, $R^1$, $R^2$, $R^3$, $R^5$, $R^6$=CH ; $R^4$, $R^{10}$=HZ=N($CH_3$)$_2$), a pale green solid which melted at 180.5° to 184.5° C. Significant infrared maxima appeared at 1615 cm$^{-1}$, 1356 cm$^{-1}$, and 823 cm$^{-1}$. An acetone solution of the product spotted onto a phenolic resin, acidic clay, and an organic acid coated paper developed a blue-colored image.

EXAMPLE 5

With stirring, a mixture of 2.91 g of 1,1-bis(4-N,N-dimethylaminophenyl)ethene, 2.16 g of 2-methyl-4-N,N-diethylaminobenzaldehyde, 2.70 g of sodium 4-methylbenzenesulfinate monohydrate in 34.0 ml of 3A ethanol and 5.0 ml of concentrated hydrochloric acid was maintained at reflux temperature for approximately nine hours. The reaction mass was poured onto an agitated mixture of 1,000 ml of water and 750.0 ml of toluene. The toluene layer was separated, washed with water, and saturated salt solution. The separated toluene layer was evaporated and the residue mixture was column chromatographed on silica gel using a toluene ethyl acetate, 3:1, eluents. The desired fractions were evaPorated to dryness and recrystallized from a mixture of hexane and isopropanol to obtain 0.76 g of 1,1-bis(4-N,N-dimethylaminophenyl)-3-(2-methyl-4-N,N-diethylaminophenyl)-3-(4-methylbenzenesulfonyl)prop-1-ene (Formula II: R, $R^1$=$C_2H_5$; $R^2$, $R^3$, $R^5$, $R^6$=$CH_3$;$R^4$, $R^{10}$=H;Z=N($CH_3$)$_2$, an off-white-colored solid which melted at 176° to 180° C. Identifying infrared absorption maxima appeared at 1610 cm$^{-1}$, 1290 cm$^{-1}$, 1150 cm$^{-1}$, 830 cm$^{-1}$, and 815 cm$^{-1}$. When an acetone solution of the product was spotted on a phenolic resin, acid clay, or organic acid coated paper, blue-colored images were produced. An acetone solution of the product and Bisphenol A was coated onto a glass plate and dried. The transmission spectrum of the coating had significant adsorptions at 735 and 780 nanometers.

EXAMPLE 6

In a manner similar to the procedure described in Example 4, a mixture of 3.0 g of 4-N,N-dimethylaminobenzaldehyde, 4.5 g of 1-phenyl-1-(4-N,N-dimethylaminophenyl)ethene, 5.0 g of sodium 4-methylbenzenesulfinate monohydrate was reacted in 75.0 ml of 3A ethanol and 5.0 ml of concentrated hydrochloric acid was interacted at reflux temperature for approximately nine hours to obtain 0.98 g of 1-phenyl-1-(4-N,N-dimethylaminophenyl)-3-(4-N,N-dimethylaminophenyl)-3-(4-methylbenzenesulfonyl)propene (Formula II: R, $R^1$, $R^3$, $R^5$, $R^6$=$CH_3$; $R^2$, $R^4$, $R^{10}$,Z=H a white solid which melted at 168° to 170° C. Significant infrared absorption maxima were observed at 1620 cm$^{-1}$, 1295 cm$^{-1}$, 1152 cm$^{-1}$, 1,828 cm$^{-1}$, and 818 cm$^{-1}$. An acetone solution of the product spotted on phenolic resin, acid clay, or organic acid coated paper developed weak green-colored images. An acetone solution of the product and Bisphenol A was coated on a glass plate and dried. The transmission spectrum of the coating had significant adsorption at 755 and 785 nanometers.

EXAMPLE 7

Proceeding in a manner similar to that described in Example 4 above, 3.8 g of 4-(piperidin-1-yl)benzaldehyde, 5.4 g of 1,1-bis(4-N,N-dimtthylaminophenyl)ethene, 5.0 g of sodium 4-methylbenzenesulfinate monohydrate, 100.0 ml of 3A ethanol, and 5.0 ml of concentrated hydrochloric acid were maintained at reflux temperature for approximately five hours to obtain 0.4 g of 1,1-bis(4-N,N-dimethyl-aminophenyl)-3-[4-(piperidin-1-yl)phenyl]-3-(4-methylbenzenesulfonyl)prop   1-ene (Formula II: R, $R^1$=piperidinyl; $R^2$, $R^4$, $R^{10}$=H; $R^3$, $R^5$, $R^6$; Z=NCCH$_3$)$_2$,=CH$_3$), a green solid melting over the range of 78° to 92° C. Significant infrared maxima appeared at 1150 cm$^{-1}$ and 830 cm$^{-1}$. An acetone solution of the product spotted onto phenolic resin, acid clay, or organic acid coated paper produced deep green-colored images. An acetone solution of the product and Bisphenol A was coated onto a glass plate and dried. The transmission spectrum of the coating had significant adsorptions at 730 and 760 nanometers.

EXAMPLE 8

A mixture consisting of 7.5 g of 4-N,N-dimethylaminobenzaldehyde, 17.1 g of 1,1-bis(1-ethyl-2-methylindol-3-yl)ethene, 8.9 g of sodium 4-methylbenzenesulfonyl monohydrate, 100.0 ml of 3A ethanol, and 5.0 ml of hydrochloric acid were combined and maintained at reflux temperature for approximately sixteen hours. Reaction was incomplete at this time, so an additional 3.4 g of (1-ethyl-2-methylindol 3-yl)ethene were added and reflux was continued for approximately six hours additional. The reaction slurry was poured onto a mixture of 1,000 ml of toluene, 1,000 ml of ice water, and 20.0 ml of ammonium hydroxide. The toluene layer containing the product was separated, washed with saturated salt solution and the toluene evaporated. The tarry residue was chromatographed on a column packed with silica gel using a toluene ethyl acetate, 3:1, eluent. The solid obtained by this method was recrystallized to obtain 0.67 g of 1,1bis(1-ethyl-2-methylindol-3-yl)-3-(4-N,N-dimethylaminophenyl)-3-(4-methylbenzenesulfonyl)prop-1-ene (Formula IV: R, $R^1$, $R^3$, $R^8$, $R^{14}$=CH$_3$; $R^2$, $R^9$, $R^{15}$=H; $R^7$, $R^{13}$=C$_2$H$_5$), a yellow solid which melted at 198° to 200° C. Significant infrared absorption maxima occurred at 1610 cm$^{-1}$, 1140 cm$^{-1}$, 1090 cm$^{-1}$, and 750 cm$^{-1}$. An acetone solution of the product spotted on phenolic resin, acid clay, or organic acid coated paper developed blue-colored images. An acetone solution of the product and Bisphenol A was coated onto a glass plate and dried. The transmission spectrum of the coating had significant adsorption at 683 and 725 nanometers.

EXAMPLE 9

A mixture of 3.0 g of 4-N,N-diethylaminobenzaldehyde, 12.0 g of 1-(4-N,N-dimethylaminophenyl)-1-(1-B-octyl-2-methylindol-3-yl)ethene, 6.0 g of sodium 4-methylbenzenesulfinate monohydrate, 100.0 ml of 3A ethanol and 8.0 ml of concentrated hydrochloric acid was maintained at reflux temperature for approximately six hours. The reaction mixture was cooled and poured into a mixture of 400.0 ml of toluene, 400.0 ml of ice water, and 100.0 ml of concentrated ammonium hydroxide. The toluene layer was separated, washed with water and saturated salt solutio,, then evaporated to dryness. The oily residue was sepa;ated by column chromatography using silica gel and eluenting first with toluene, then with 1:3 ethyl acetate:toluene solution to obtain 0.41 g of 1-(4-N,N-dimethylaminophenyl)-1-(1-n-octyl-2-methyl-indol-3-yl)-3-(4-N,N-diethylinophenyl)-3-(4-methylbenzenesulfonyl)prop-1-ene (Formula III: R, $R^1$=C$_2$H$_5$; $R^2$, $R^4$, $R^{15}$=H; $R^3$, $R^5$, $R^6$, $R^{14}$=CH$_3$; $R^{13}$=n-C$_8$H$_{17}$), an oil with significant infrared absopption maxima at 1610 cm$^{-1}$, 1140 cm$^{-1}$, and 750 cm$^{-1}$. An acetone solution of the product spotted on phenolic resin, acid clay, or organic acid coated papers developed blue-green to blue-black-colored images. An acetone solution of the product and Bisphenol A was coated onto a glass plate and dried. The transmission spectrum of the coating had significant adsorption at 660 and 770 nanometers.

It is contemplated that by following procedures similar to those described in Examples 1 to 7 above but employing the appoopriately substituted 2-R$^2$-4-N-R-N-R$^1$-aminobenzaldehyde with the appropriately substituted 1-(2-R$^4$-4-N-R$^5$-N-R$^6$-aminophenyl)-1-(2-R$^{10}$-4-Z-phenyl) ethene and sodium 4-R$^3$-benzenesulfinate there will be obtained the appropriate 1-(2-R$^4$-4-N-R$^5$-N-R$^6$-aminophenyl)-1-(2-R$^{10}$-4-Z-phenyl)3-(2-R$^2$-4-N-R-N-R$^1$-aminophenyl)-3-(4-R$^3$-benzenesulfonyl) propene of Formula II, Examples 10 to 27 presented in Table 1 hereinbelow.

TABLE VI 1-(2-R$^4$—4-N—R$^5$—N—R$^6$—Aminophenyl)-1-(2-R$^{10}$—Z—phenyl)-3-(2-R$^2$—4-N—R—N—R$^1$—aminophenyl)-3-(4-R$^3$—benzenesulfonyl) of propenes of Formula II

| EX. | R | $R^1$ | $R^2$ | $R^3$ | $R^4$ | $R^5$ | $R^6$ | $R^{10}$ | Z |
|---|---|---|---|---|---|---|---|---|---|
| 10 | C$_4$H$_9$ | C$_4$H$_9$ | CH$_3$O | C$_{12}$H$_{25}$ | CH$_3$ | C$_2$H$_5$ | C$_2$H$_5$ | C$_2$H$_5$ | N(C$_2$H$_5$)$_2$ |
| 11 | C$_8$H$_{17}$ | C$_8$H$_{17}$ | CH$_3$ | Cl | C$_2$H$_5$ | C$_6$H$_5$CH$_2$ | C$_2$H$_5$ | CH$_3$ | N(C$_4$H$_9$)$_2$ |
| 12 | C$_6$H$_5$CH$_2$ | C$_2$H$_5$ | Cl | NO$_2$ | CH$_3$O | 4-CH$_3$C$_6$H$_4$CH$_2$ | H | CH$_3$O | N(C$_6$H$_5$)(CH$_3$) |
| 13 | C$_6$H$_{13}$ | C$_6$H$_{13}$ | F | C$_8$H$_{17}$ | C$_4$H$_9$O | CH$_3$ | CH$_3$ | Cl | N(C$_2$H$_5$)(C$_6$H$_5$CH$_2$) |
| 14 | 4-CH$_3$C$_6$H$_4$CH$_2$ | H | NO$_2$ | C$_2$H$_5$ | C$_8$H$_{17}$ | C$_6$H$_5$ | C$_2$H$_5$ | Br | N(C$_8$H$_{17}$)$_2$ |
| 15 | 4-ClC$_6$H$_4$CH$_2$ | CH$_3$ | C$_2$H$_5$ | C$_4$H$_9$ | F | C$_4$H$_9$ | C$_4$H$_9$ | NO$_2$ | N(C$_6$H$_5$CH$_2$)$_2$ |
| 16 | 4-CH$_3$OC$_6$H$_4$CH$_2$ | C$_3$H$_7$ | C$_4$H$_9$ | H | C$_2$H$_5$O | C$_8$H$_{17}$ | C$_8$H$_{17}$ | C$_4$H$_9$O | H |
| 17 | C$_{12}$H$_{25}$ | C$_{12}$H$_{25}$ | C$_8$H$_{17}$O | C$_2$H$_5$ | Cl | 4-ClC$_6$H$_4$CH$_2$ | H | C$_{12}$H$_{25}$ | H |
| 18 | C$_{16}$H$_{33}$ | C$_{16}$H$_{33}$ | CH$_3$ | C$_{12}$H$_{25}$ | C$_8$H$_{17}$O | 3-NO$_2$C$_6$H$_4$CH$_2$ | CH$_3$ | C$_8$H$_{17}$O | N(C$_2$H$_5$) |
| 19 | C$_6$H$_5$CH$_2$ | C$_4$H$_9$ | Br | Br | C$_{12}$H$_{25}$ | C$_4$H$_9$ | C$_4$H$_9$ | Br | N(CH$_3$)(CH$_3$C$_6$H$_4$) |
| 20 | 2,4-(CH$_3$)$_2$C$_6$H$_3$CH$_2$ | H | Cl | C$_3$H$_7$ | C$_4$H$_9$ | C$_{16}$H$_{33}$ | H | C$_4$H$_9$ | H |
| 21 | C$_6$H$_5$ | C$_2$H$_5$ | NO$_2$ | C$_4$H$_9$ | Cl | C$_6$H$_5$CH$_2$ | C$_2$H$_5$ | C$_8$H$_{17}$ | N(CH$_3$)$_2$ |
| 22 | 4-CH$_3$C$_6$H$_5$ | CH$_3$ | C$_4$H$_9$O | Cl | C$_2$H$_5$ | C$_{16}$H$_{33}$ | C$_{16}$H$_{33}$ | F | N(C$_2$H$_5$)$_2$ |
| 23 | 4-CH$_3$OC$_6$H$_4$ | C$_2$H$_5$ | C$_3$H$_7$ | C$_2$H$_5$ | CH$_3$ | 2,4(CH$_3$)$_2$C$_3$H$_2$CH | H | C$_{16}$H$_{33}$ | H |
| 24 | 3-NO$_2$C$_6$H$_4$CH$_2$ | H | CH$_3$ | C$_4$H$_9$ | Br | C$_4$H$_9$ | C$_4$H$_9$ | C$_2$H$_5$ | N(CH$_3$)(C$_6$H$_5$) |
| 25 | C$_{14}$H$_{29}$ | C$_{14}$H$_{29}$ | C$_6$H$_{13}$O | F | C$_8$H$_{17}$ | 4-CH$_3$OC$_6$H$_4$CH$_2$ | C$_2$H$_5$ | C$_2$H$_5$O | NHC$_6$H$_5$ |
| 26 | C$_4$H$_9$ | C$_2$H$_5$ | C$_{12}$H$_{25}$ | Br | C$_4$H$_9$O | C$_6$H$_5$ | CH$_3$ | CH$_3$ | H |

TABLE VI-continued 1-(2-$R^4$—4-N—$R^5$—N—$R^6$—Aminophenyl)-1-(2-$R^{10}$—Z—phenyl)-3-
(2-$R^2$—4-N—R—N—$R^1$—aminophenyl)-3-(4-$R^3$—benzenesulfonyl) of propenes of Formula II

| EX. | R | $R^1$ | $R^2$ | $R^3$ | $R^4$ | $R^5$ | $R^6$ | $R^{10}$ | Z |
|---|---|---|---|---|---|---|---|---|---|
| 27 | 3-$NO_2C_6H_4$ | $CH_3$ | $C_4H_9$ | $C_{12}H_{25}$ | $NO_2$ | 4-$CH_3C_6H_5$ | $C_2H_5$ | $NO_2$ | $N(C_{16}H_{33})_2$ |

It is contemplated that by following procedure similar to that described in Example 9 above but employing the appropriately substituted 2-$R^2$-4-N-R-N-$R^1$-aminobenzaldehyde with the appropriately 1-(2-$R^4$-H-$R^5$-N-$R^6$-aminophenyl)-1-(1-$R^{13}$-2-$R^{14}$-5/6-$R^{15}$-indol-3-yl)ethene and sodium 4-$R^3$-benzenesulfinate there will be obtained the appropriate 1-(2-$R^4$-4-N-$R^5$-N-$R^6$-aminophenyl)-1-(1-$R^{13}$-2-$R^{14}$-5/6-$R^{15}$-indol-3-yl)-3-(2-$R^3$-benzenesulfonyl) propene of Formula III, Examples 28 to 45 present in Table II hereinbelow.

TABLE II 1-(2-$R^4$—4-N—$R^5$—N—$R^6$—Aminophenyl)-1-(1-$R^{13}$—2-$R^{14}$—5/6-$R^{15}$—indol-3-yl)-3-
(2-$R^2$—4-N—R—N—$R^1$—aminophenyl)-3-(4-$R^3$—benzenesulfonyl)propene of Formula III

| EX. | R | $R^1$ | $R^2$ | $R^3$ | $R^4$ | $R^5$ | $R^6$ | $R^{13}$ | $R^{14}$ | $R^{15}$ |
|---|---|---|---|---|---|---|---|---|---|---|
| 28 | 3-$NO_2C_6H_4$ | $CH_3$ | $CH_3O$ | $C_{12}H_{25}$ | $NO_2$ | $C_2H_5$ | $C_2H_5$ | $C_6H_5OC_2H_4$ | H | 5-$CH_3$ |
| 29 | $C_4H_9$ | $C_2H_5$ | $CH_3$ | Cl | $C_4H_9O$ | $C_6H_5CH_2$ | $C_2H_5$ | $C_8H_{17}$ | $C_2H_5$ | 5-F |
| 30 | $C_{14}H_{29}$ | $C_{14}H_{29}$ | Cl | $NO_2$ | $C_8H_{17}$ | 4-$CH_3C_6H_4CH_2$ | H | $C_4H_9$ | $C_3H_7$ | 6-$NO_2$ |
| 31 | 3-$NO_2C_6H_4CH_2$ | H | F | $C_8H_{17}$ | Br | $CH_3$ | $CH_3$ | $C_{10}H_{33}$ | $CH_3$ | 5-$CH_3O$ |
| 32 | 4-$CH_3OC_6H_4$ | $C_2H_5$ | $NO_2$ | $C_2H_5$ | $CH_3$ | $C_2H_5$ | $C_2H_5$ | $C_2H_5OC_2H_4$ | H | 6-$NO_2$ |
| 33 | 4-$CH_3C_6H_5$ | $CH_3$ | $C_2H_5$ | $C_4H_9$ | $C_2H_5$ | $C_4H_9$ | $C_4H_9$ | $C_6H_4CH_2$ | $C_4H_9$ | H |
| 34 | $C_6H_5$ | $C_2H_5$ | $C_4H_9$ | H | Cl | $C_8H_{17}$ | $C_8H_{17}$ | 4-$CH_3C_6H_4CH_2$ | $C_6H_5$ | 5-$NO_2$ |
| 35 | 2,4-$(CH_3)_2C_6H_3CH_2$ | H | $C_8H_{17}O$ | $C_2H_5$ | $C_4H_9$ | 4-$ClC_6H_4CH_2$ | H | $C_{12}H_{25}$ | $C_2H_5$ | 5-Br—6-$NO_2$ |
| 36 | $C_6H_5CH_2$ | $C_4H_9$ | $CH_3$ | $C_{12}H_{25}$ | $C_{12}H_{25}$ | 3-$NO_2C_6H_4CH_2$ | $CH_3$ | $C_9H_{19}$ | $C_4H_9$ | 5,6-$(CH_3)_2$ |
| 37 | $C_{16}H_{33}$ | $C_{16}H_{33}$ | Br | Br | $C_8H_{17}O$ | $C_4H_9$ | $C_4H_9$ | 4-$CH_3OC_6H_4CH_2$ | $C_6H_5$ | 6-Br |
| 38 | $C_{12}H_{25}$ | $C_{12}H_{25}$ | Cl | $C_3H_7$ | Cl | $C_{16}H_{33}$ | H | $C_{14}H_{29}$ | H | 6-Cl |
| 39 | 4-$CH_3OC_6H_4CH_2$ | $C_3H_7$ | $NO_2$ | $C_4H_9$ | $C_2H_5O$ | $C_6H_5CH_2$ | $C_2H_5$ | 4-$ClC_6H_4CH_2$ | $C_3H_7$ | 5-$CH_3$ |
| 40 | 4-$ClC_6H_4CH_2$ | $CH_3$ | $C_4H_9O$ | Cl | F | $CH_3$ | $C_{16}H_{33}$ | $C_5H_{11}$ | $C_4H_9$ | 6-Cl |
| 41 | 4-$CH_3C_6H_4CH_2$ | H | $C_3H_7$ | $C_2H_5$ | $C_8H_{17}$ | 2,4-$(CH_3)_2C_6H_3CH_2$ | H | $C_8H_{17}$ | $C_2H_5$ | 6-$CH_3$ |
| 42 | $C_6H_{13}$ | $C_6H_{13}$ | $CH_3$ | $C_4H_9$ | $C_4H_9$ | $C_4H_9$ | $C_4H_9$ | 2,4-$(CH_3O)_2C_6H_3CH_2$ | H | 6-F |
| 43 | $C_6H_5CH_2$ | $C_2H_5$ | $C_6H_{13}O$ | F | $CH_3O$ | 4-$CH_3OC_6H_4CH_2$ | $C_2H_5$ | $C_6H_{13}$ | $C_6H_5$ | 5-$CH_3O$ |
| 44 | $C_8H_{17}$ | $C_8H_{17}$ | $C_{12}H_{25}$ | Br | $C_2H_5$ | $C_6H_5$ | $CH_3$ | 3-$NO_2C_6H_4CH_2$ | $CH_3$ | 6-$CH_3O$ |
| 45 | $C_4H_9$ | $C_4H_9$ | $C_4H_9$ | $C_{12}H_{25}$ | $CH_3$ | 4-$CH_3C_6H_5$ | $C_2H_5$ | $C_8H_{17}$ | $C_2H_5$ | H |

It is contemplated that by following procedure similar to that described in Example 9 above but employing the appropriately substituted 2-$R^2$-4-N-R-N-$R^1$-aminobenzaldehyde with the appropriately substituted 1-(1-$R^7$-2-$R^8$-5/6-$R^9$-indol-3-yl)-1-(1-$R^{13}$-2-$R^{14}$-5/6-$R^{15}$-indol-3-yl)ethene and sodium 4-$R^3$-benzenesulfinate there will be obtained the appropriate 1-(1-$R^7$-2-$R^8$-5/6$R^9$-indol-3-yl)-1-(1-$R^{13}$-2-$R^{14}$-5/6-$R^{15}$-indol-3-yl)-3-(2-$R^2$-4-N-R-N-$R^1$-aminophenyl)-3-(4-$R^3$-benzenesulfonyl)propene of Formula IV, Examples 46 to 63 presented in Table III hereinbelow.

TABLE III 1-(1-$R^7$—2-$R^8$—5/6-$R^9$—indol-3-yl)-1-(1-$R^{13}$—2-$R^{14}$—5/6-$R^{15}$—indol-3-yl)-3-
(2-$R^2$—4-N—R—B—$R^1$—aminophenyl)-3-(4-$R^3$—benzenesulfonyl)propene

| EX. | R | $R^1$ | $R^2$ | $R^3$ | $R^7$ | $R^8$ | $R^9$ | $R^{13}$ | $R^{14}$ | $R^{15}$ |
|---|---|---|---|---|---|---|---|---|---|---|
| 46 | $C_4H_9$ | $C_4H_9$ | $C_4H_9$ | $C_{12}H_{25}$ | H | $CH_3$ | H | H | $CH_3$ | H |
| 47 | $C_8H_{17}$ | $C_8H_{17}$ | $C_{12}H_{25}$ | Br | H | $C_6H_5$ | H | H | $C_6H_5$ | H |
| 48 | $C_6H_5CH_2$ | $C_2H_5$ | $C_6H_{13}O$ | F | $C_6H_5CH_2$ | H | 5-F | $C_6H_5CH_2$ | H | 5-F |
| 49 | $C_6H_{13}$ | $C_6H_{13}$ | $CH_3$ | $C_4H_9$ | $CH_3$ | H | 6-$NO_2$ | $CH_3$ | H | 6-$NO_2$ |
| 50 | 4-$CH_3C_6H_4CH_2$ | H | $C_3H_7$ | $C_2H_5$ | $C_8H_{17}$ | $CH_3$ | H | $C_8H_{17}$ | $CH_3$ | H |
| 51 | 4-$ClC_6H_4CH_2$ | $CH_3$ | $C_4H_9$ | Cl | $C_4H_9$ | $C_2H_5$ | 5-Br | $C_4H_9$ | $C_2H_5$ | 5-Br |
| 52 | 4-$CH_3C_6H_4CH$ | $C_3H_7$ | $NO_2$ | $C_4H_9$ | $C_4H_9$ | H | 5-$CH_3O$ | $C_4H_9$ | H | 5-$CH_3O$ |
| 53 | $C_{12}H_{25}$ | $C_{12}H_{25}$ | Cl | $C_3H_7$ | H | $C_2H_5$ | 5-$CH_3$ | H | $C_2H_5$ | 5-$CH_3$ |
| 54 | $C_{16}H_{33}$ | $C_{16}H_{33}$ | Br | Br | $CH_3$ | H | 5-Br—6-$NO_2$ | $CH_3$ | H | 5-Br—6-$NO_2$ |
| 55 | $C_6H_5CH_2$ | $C_4H_9$ | $CH_3$ | $C_{12}H_{25}$ | H | $CH_3$ | 5,6-$(CH_3)_2$ | H | $CH_3$ | 5,6-$(CH_3)_2$ |
| 56 | 2,4-$(CH_3)_2C_6H_3CH_2$ | H | $C_8H_{17}O$ | $C_2H_5$ | $C_{12}H_{25}$ | $CH_3$ | H | $C_{12}H_{25}$ | $CH_3$ | H |
| 57 | $C_6H_5$ | $C_2H_5$ | $C_4H_9$ | H | $C_{16}H_{33}$ | $CH_3$ | H | H | $CH_3$ | 6-Br |
| 58 | 4-$CH_3C_6H_5$ | $CH_3$ | $C_2H_5$ | $C_4H_9$ | H | $C_6H_5$ | 6-Cl | H | $C_2H_5$ | 6-$CH_3$ |
| 59 | 4-$CH_3OC_6H_4$ | $C_2H_5$ | $NO_2$ | $C_2H_5$ | 4-$BrC_6H_4CH_2$ | $CH_3$ | H | $C_2H_5$ | $CH_3$ | H |
| 60 | 3-$NO_2C_6H_4CH_2$ | H | F | $C_8H_{17}$ | $C_6H_{13}$ | $C_3H_7$ | 6-$CH_3$ | $C_6H_{13}$ | $C_3H_7$ | 6-$CH_3$ |
| 61 | $C_{14}H_{29}$ | $C_{14}H_{29}$ | Cl | $NO_2$ | 3-$ClC_6H_4CH_2$ | $C_2H_5$ | H | $C_2H_5$ | $CH_3$ | H |
| 62 | $C_4H_9$ | $C_2H_5$ | $CH_3$ | Cl | $C_6H_5CH_2$ | H | 5-F | $C_6H_5CH_2$ | H | 5-F |
| 63 | 3-$NO_2C_6H_4$ | $CH_3$ | $CH_3O$ | $C_{12}H_{25}$ | $C_{10}H_{21}$ | $CH_3$ | H | $C_{10}H_{21}$ | $CH_3$ | H |

EXAMPLE 64

The use of compounds of Formulas I, II, III, and IV, described in the foregoing examples, as color-forming components in pressure-sensitive microencapsulated copying systems is illustrated by the incorporation and testing of the compound of Example 1, 1,1-bis(4-N,N-dimethylaminophenyl)-3-(4-N,N-dimethylaminophenyl)-3-(4-methylbenzenesulfonyl)prop-1-ene in a pressure-sensitive marking paper. The test paper was Prepared by a procedure similar to that described in U.S. Pat. No. 4,275,905.

A. A mixture of 7.8 g of 10 percent aqueous EMA 31 (ethylene maleic anhydride copolymer with a molecular weight range of 75,000 to 90,000, supplied by Monsanto Chemical Co.), 14.5 g of 10 percent aqueous EMA 1104 (ethylene maleic anhydrideccopolymer with a molecular weight range of 5,000 to 7,000, supplied by Monsanto Chemical Co.), 78.0 ml of distilled water was adjusted to pH 4.0 with the addition of 25 percent aqueous sodium hydroxide. A solution was prepared by dissolving 1.2 g of 1,1-bis(4-N,N-dimethylaminophenyl)-3-(4-N,N-dimethylaminophenyl)-3-(4-methylbenzenesulfonyl)prop-1-ene in 58.8 g of an alkylbenzene. This solution was added to the aqueous mixture and the resulting mixture was emulsified using a variable speed one-half horsepower Eppenbach Homomixer (Gifford Wood Co., Hudson, NY) at an applied voltage of 60 volts until droplets are smaller than 5 microns. While maintaining the rapid agitation, 22.5 g of 50 percent aqueous Resimene 714 (methylated methylol melamine resin, supplied by Monsanto Chemical Co.) was added over approximately three to five minutss. After the microcapsules had formed, the suspension was transferred to a round bottom flask equipped with a conventional blade-type laboratory agitator and stirred approximately two hours at 50° C. The mixture was then stirred overnight at ambient temperature. The mixture was adjusted to PH 7.0 with the addition concentrated aqueous sodium hydroxide.

B. The microcapsule suspension prepared in part A above was coated on paper sheets to a thickness of approximately 0.0015 inch and the coated sheets of paper air dried. The paper thus coated with the microencapsulated colorless precursor was assembled as the top sheet in a manifold system by positioning the coated side in contact with a color developer of the electron-accepting type. More specifically, papers coated with a phenolic resin, organic and or with an acidic clay were employed in this test. An image was then drawn with a stylus on the top sheet bearing the microencapsulated colorless precursor on its reverse side causing the effected microcapsules to rupture thus allowing the solution of the colorless precursor held by said microcapsules to flow into contact with the color-developing substance on the receiving sheet whereupon a color image immediately formed. On the acidic clay receiving sheet the image was a blue color. On the phenolic resin receiving sheet the image was a blue color. Both developed images exhibited excellent light stability and near infrared absorption when developed at 775 nm.

EXAMPLE 65

The utility of the compounds of Formulas I, II, III, and IV as color-forming components in thermal marking systems is illustrated by the incorporation and testing o the compound of Example 1, 1,1-bis (4-N,N-dimethylaminophenyl)-3-(4-N,N-dimethylaminophenyl)-3-(4-methylbenzenesulfonyl)propene in a thermal-responsive marking paper. The test paper was prepared by a procedure similar to that described in U.S. Pat. No. 3,539,375.

A. A mixture of 2.0 g of 1,1-bis(4-N,N-dimethylaminophenyl)-3(4N,N dimethylaminophenyl)-3-(4-methylbenzenesulfonyl)propene of a 10 percent aqueous solution of polyvinyl alcohol (approximately 99 percent hydrolyzed), 8.6 g of distilled water and 31.6 g of 1/16 inch diameter zirconium grinding beads was charged into a container which was placed in a mechanical shaker. Shaking was effected for one hour. The zirconium beads were then removed by straining the mixture through a No. 40 sieve.

B. Similarly. a mixture of 9.8 g of 4,4'-isopropylidine diphenol (Bisphenol A), 42.0 g of a 10 percent aqueous polyvinyl alcohol solution (approximately 99 percent hydrolyzed), 18.2 g of water and 221.1 g of 1/16 inch diameter zirconium grinding beads was charged into a container which was placed in a mechanical shaker. After shaking was effected for one hour, the zirconium beads were removed by straining through a No. 40 sieve.

C. A coating composition was prepared by mixing 2.5 g of the slurry from Part A and 22.5 g of the slurry from Part B. The mixture was then uniformly coated on sheets of paper at a thickness of approximately 0.0015 inch and the coated sheets air dried. The coated paper placed on a smooth flat surface with a stylus heated to approximately 125° C. An intense cyan-colored image corresponding to the traced design promptly developed.

What is claimed is:

1. A substrate for use in transfer imaging comprising a support sheet coated with a layer containing as a color-forming substance a 1-A-1-B-3-(2-$R^2$-4-N-R-N-$R^1$-aminophenyl)-3-(4-$R^3$-phenylsulfonyl)-prop-1-ene having the formula

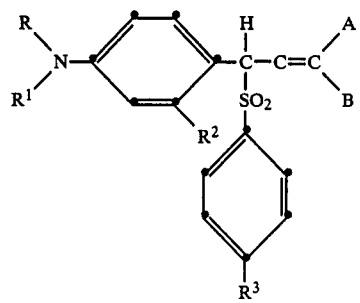

wherein:
A represents a moiety selected from the group consisting of

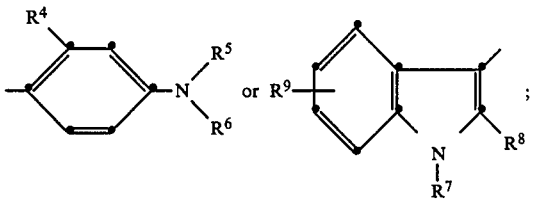

B represents a moiety selected from the group consisting of

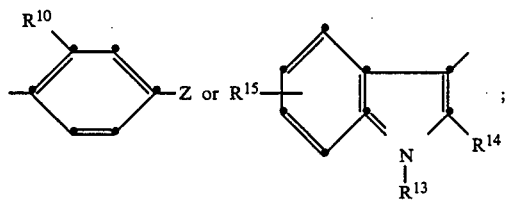

in which:
Z, represents—$NR^{11}R^{12}$;
R, $R^5$ and $R^{11}$ independently represent hydrogen; non-tertiary $C_1$ to $C_{16}$ alkyl; phenyl; phenyl substituted by one or two of non-tertiary $C_1$ to $C_4$ alkyl, non-tertiary $C_1$ to $C_4$ alkoxy, nitro or halo; benzyl; or benzyl substituted in the benzene ring by one or two of non-tertiary $C_1$ to $C_4$ alkyl, non-tertiary $C_1$ to $C_4$ alkoxy, nitro or halo;

$R^1$, $R^6$ and $R^{12}$ independently represent non-tertiary $C_1$ to $C_{16}$ alkyl;

$R^2$, $R^4$ and $R^{10}$ independently represent hydrogen, nontertiary $C_1$ to $C_{16}$ alkyl, non-tertiary $C_1$ to $C_8$ alkoxy, nitro or halo;

$R^3$, represents hydrogen, non-tertiary $C_1$ to $C_{16}$ alkyl, non-tertiary $C_1$ to $C_4$ alkoxy, nitro or halo;

$R^7$ and $R^{13}$ independently represent hydrogen; or nontertiary $C_1$ to $C_{16}$ alkyl unsubstituted or substituted by non-tertiary $C_1$ to $C_{16}$ alkoxy, phenoxy, phenyl, phenyl substituted by one or two of non-tertiary $C_1$ to $C_4$ alkyl, non-tertiary $C_1$ to $C_4$ alkoxy, nitro or halo;

$R^8$ and $R^{14}$ independently represent hydrogen, non-tertiary $C_1$ to $C_4$ alkyl or phenyl;

$R^9$ and $R^{15}$ independently represent one or two of hydrogen, non-tertiary $C_1$ to $C_4$ alky, nontertiary $C_1$ to $C_4$ alkoxy, nitro of halo; and wherein R and $R^1$ together with the nitrogen represent piperdinyl or pyrrolindinyl.

2. A substrate for use in transfer imaging comprising a support sheet coated with a layer containing as a color-forming substance a 1-(2-$R^4$-4-N-$R^5$-N-$R^6$-aminophenyl)-1-(2-$R^{10}$-N-$R^{11}$-N-$R^{12}$-aminophenyl)-3-(2-$R^2$-4-N-R-N-$R^1$-aminophenyl)-3-(4-$R^3$-phenylsulfonyl)prop-1-ene according to claim 1.

3. A substrate for use in transfer imaging comprising a support sheet coated with a layer containing as a color-forming sbstance a 1-(2-$R^4$-4-N-$R^5$-N-$R^6$-aminophenyl)-1-(I-$R^{13}$-2-$R^{14}$-5/6-$R^{15}$-INDO-3-yl) -3-(2-$R^2$-4-N-R-N-$R^1$-aminophenyl)-3-(4-$R^3$-phenylsulfonyl)prop-1-ene according to claim 1.

4. A substrate for use in transfer imaging comprising a support sheet coated with a layer containing as a color-forming substance a 1-(1-$R^7$-2-$R^8$-5/6-$R^9$-indol-3-yl)-1-(l-$R^{13}$-2-$R^{14}$-5/6-$R^{15}$-INDOL-3-yl)-3-(2-$R^2$-4-N-R-N-$R^1$-aminophenyl)-3-(4-$R^3$-phenylsulfonyl)-prop-1-ene according to claim 1.

5. A substrate for use in a pressure-sensitive or thermal-responsive marking system comprising a support sheet coated with a layer containing as a color-forming substance a 1-A-1-B-3-(2-$R^2$-4-N-R-N-$R^1$-aminophenyl)-3-(4-$R^3$-phenyl-sulfonyl)prop-1-ene having the formula

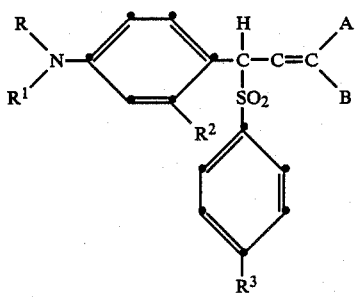

wherein:

A represents a moiety selected from the group consisting of

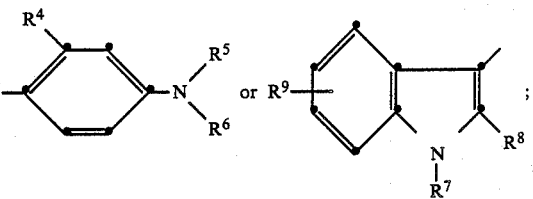

B represents a moiety selected from the group consisting of

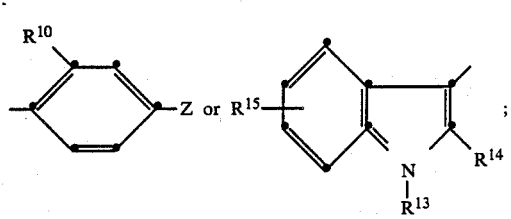

in which:

Z represents $-NR^{11}R^{12}$;

R, $R^5$ and $R^{11}$ independently represent hydrogen; non-tertiary $C_1$ to $C_{16}$ alkyl; phenyl; phenyl substituted by one or two of non-tertiary $C_1$ to $C_4$ alky, non-tertiary $C_1$ to $C_4$ alkoxy, nitro or halo; benzyl; or benzly substituted in the benzene ring by one or two of non-tertiary $C_1$ to $C_4$ alkyl, non-tertiary $C_1$ to $C_4$ alkoxy, nitro or halo;

$R^1$, $R^6$ and $R^{12}$ independently represent non-tertiary $C_1$ to $C_{16}$ alkyl;

$R^2$, $R^4$ and $R^{10}$ independently represent hydrogen, non-tertiary $C_1$ to $C_{16}$ alkyl, non-tertiary $C_1$ to $C_8$ alkoxy, nitro or halo;

$R^3$ represents hydrogen, non-tertiary $C_1$ to $C_{16}$, alkyl, non-tertiary $C_1$ to $C_4$ alkoxy, nitro or halo;

$R^7$ and $R^{13}$ independently represent hydrogen; or non-tertiary $C_1$ to $C_{16}$ alkyl unsubstituted or substituted by non-teriatry $C_1$ to $C_{16}$ alkoxy, phenoxy, phenyl, phenyl substituted by one or two of non-tertiary $C_1$ to $C_4$ alkyl, non-tertiary $C_1$ to $C_4$ alkoxy, nitro or halo;

$R^8$ and $R^{14}$ independently represent hydrogen, non-tertiary $C_1$ to $C_4$ alkyl or phenyl;

$R^9$ and $R^{15}$ independently represent one or two of hydrogen, non-tertiary $C_1$ to $C_4$ alkoxy, nitro or halo; and wherein R and $R^1$ together with the nitrogen represent piperdinyl or pyrrolidinyl.

6. A substrate for use in a pressure-sensitive or thermal-responsive marking system comprising a support sheet coated with a layer containing as a color-forming substance a 1-(2-$R^4$-4-N-$R^5$-N-$R^6$-aminophenyl)-1-(2-$R^{10}$-4-N-$R^{11}$-N-$R^{12}$-aminophenyl)-3-(2-$R^2$-4-N-R-N-$R^1$-aminophenyl)-3-(4-$R^3$-phenylsulfonyl)prop-1-ene according to claim 5.

7. A substrate for use in a pressure-sensitive or thermal-responsive marking system comprising a support sheet coated with a layer containing as color-forming substance a 1-(2-$R^4$-4-N-$R^5$-N -$R^6$-aminophenyl)-1-(l-$R^{13}$-2-$R^{14}$-5/6-$R^{15}$-indol-3-yl)-3-(2-$R^2$-4-N-R-N-$R^1$-aminophenyl)-3-(4-$R^3$-phenylsulfonyl)prop-1-ene according to claim 5.

8. A substrate for use in a pressure-sensitive or thermal-responsive marking system comprising a support sheet coated with a layer containing as a color-forming substance a 1-(1-$R^7$-2-$R^8$-5/6-$R^9$-indol-3-yl)-1-(1-$R^{13}$-2-$R^{14}$-5/6-$R^{15}$-indol-3-yl)-3-(2-$R^2$-4-N-R-N-$R^1$-aminophenyl)-3-(4-$R^3$-phenylsulfonyl)prop-1-ene according to claim 5.

9. A pressure-sensitve transfer sheet according to claim 5 adapted for use with a receiving sheet having an electron-accepting layer, comprising a support sheet coated on one side with a layer of pressure-rupturable microcapsules, said microcapsoles containing a liquid solution of a color-forming substance comprising at least one 1-A-1-B-3-(2-$R^2$-4-N-R-N-$R^1$-aminophenyl)-3-(4-$R^3$-phenylsulfonyl) prop-1-ene.

10. A termal-responsive according to claim 5 comprising a support sheet coated on one side with a layer containing a mixture comprising as least one color-forming compound A-1-A-1-B-3-(2-$R^2$-4-N-R-N-$R^1$-aminophenyl-3-4-$R^3$-phenylsulfonyl)prop-l-ene and an acidic developer arranged such that application of heat will produce a mark-forming reaction between the color-forming compound and the acidic developer.

* * * * *